United States Patent
Feng

(10) Patent No.: US 9,149,649 B2
(45) Date of Patent: Oct. 6, 2015

(54) SEMICONDUCTOR LASER BLOOD OXYGEN THERAPEUTIC APPARATUS

(75) Inventor: Yonghua Feng, Hubei Province (CN)

(73) Assignee: WUHAN HNC TECHNOLOGY CO., LTD., Hubei Province (CN)

(*) Notice: Subject to any disclaimer, the term of this patent is extended or adjusted under 35 U.S.C. 154(b) by 574 days.

(21) Appl. No.: 13/634,879

(22) PCT Filed: Jan. 31, 2011

(86) PCT No.: PCT/CN2011/070836
§ 371 (c)(1),
(2), (4) Date: Sep. 14, 2012

(87) PCT Pub. No.: WO2011/140845
PCT Pub. Date: Nov. 17, 2011

(65) Prior Publication Data
US 2013/0008435 A1    Jan. 10, 2013

(51) Int. Cl.
*A61M 16/00* (2006.01)
*A61N 5/06* (2006.01)
*A61N 5/067* (2006.01)

(52) U.S. Cl.
CPC .............. *A61N 5/0613* (2013.01); *A61M 16/00* (2013.01); *A61N 2005/067* (2013.01); *A61N 2005/0668* (2013.01)

(58) Field of Classification Search
CPC ..... A61N 5/0613; A61N 5/06; A61N 5/0601; A61N 5/0602; A61N 5/0603; A61N 2005/0604; A61N 2005/0607; A61N 2005/0606; A61N 2005/0612; A61M 16/0063; A61M 16/0057; A61M 16/10; A61M 16/00
See application file for complete search history.

(56) References Cited

U.S. PATENT DOCUMENTS

| | | | | |
|---|---|---|---|---|
| 892,441 | A | * | 7/1908 | Metzler .......................... 607/80 |
| 2,213,403 | A | * | 9/1940 | Miller ..................... 128/202.25 |
| 8,535,361 | B2 | * | 9/2013 | Lim et al. ........................ 607/89 |

FOREIGN PATENT DOCUMENTS

| | | | |
|---|---|---|---|
| CN | 1174089 A | * | 2/1998 |
| CN | 1555896 A | * | 12/2004 |

* cited by examiner

*Primary Examiner* — Valerie L Skorupa

(57) ABSTRACT

A semiconductor laser blood oxygen therapeutic apparatus comprising a host (32); a terminal being an oxygen output terminal, a laser irradiating terminal and an ozone output terminal (48), a laser generator located in a therapeutic terminal (34); the oxygen output terminal includes an oxygen absorbing device (25) and a laser-oxygen two-in-one therapeutic device (27); the laser-oxygen two-in-one therapeutic device (27) is provided with a two-in-one nasal clip (31); the oxygen absorbing device (25) is provided with a detachable atomization pressure decreasing device (24), while the host (32) is provided with a security identifying device which identifies the external atomization pressure decreasing device automatically; and an ozone generating cabin (36) is connected between a relief pressure valve (20) and a humidifying bottle (9).

10 Claims, 7 Drawing Sheets

SEMICONDUCTOR LASER BLOOD OXYGEN THERAPEUTIC APPARATUS

BACKGROUND OF THE INVENTION

The present invention relates to a medical instrument, and specifically to a semiconductor laser blood oxygen therapeutic apparatus that is suitable for household.

The method of treatment of diseases by making use of laser irradiation of blood and blood oxygenation to cause biological effects and photochemical reaction is called the "laser blood oxygen therapy". There are the following three representative instruments adopting this method of treatment of diseases.

The first instrument is represented by the laser quantum blood vitro radiation therapeutic apparatus disclosed by the Chinese patent application CN1099300A with an application number 94107164.2, which is used to irradiate a patient's in vitro blood simultaneously with the He—Ne laser and ultraviolet light and oxygenate the blood and then transfuse the irradiated blood into the patient, so as to achieve the purpose of treatment of the patient. This therapeutic apparatus can also play a role in the treatment; however, because there need to be many times of blood drawing or puncture of a needle into the blood vessel during the treatment, which may inevitably result in wounds of the patient's blood vessels and skin, the patient is hard to accept this therapeutic apparatus; meanwhile, because there need to be many times of blood drawing or puncture of a needle into the blood vessel, a cross infection is easy to be caused.

The second instrument is represented by the noninvasive laser irradiation therapeutic apparatus disclosed by the Chinese patent application CN1174089A with an application number 96117068.9, which uses the red laser of 630-670 nm in wavelength to irradiate the patient's oral mucosal blood accompanied by oxygen inhalation for the treatment of a variety of hypoxic ischemic cardiovascular and cerebrovascular diseases. Although this invention needs no blood, will not damage the patient's blood vessels and skin, needs no sterile room, and is easy for the medical personnel to operate, it is subject to separation of the laser therapeutic apparatus from the oxygen supply device, poor portability, space, location, irradiated sites, single function and the like, and the patient is easy to suffer from nausea and vomiturition in the process of treatment with it, making a part of the patients not easy to accept or keep the treatment. Both of the above two methods, although having very good verified clinical curative effects, have basically been eliminated for being subject to a variety of factors.

The third instrument is represented by the laser oxygen machine disclosed by the Chinese patent application CN1555896A with an application number 200410021690,5, which combines the laser therapeutic apparatus and the oxygen generator into one, avoiding the disadvantages of the first two methods and overcoming the defects of space and single function. However, the laser-oxygen two-in-one therapeutic head of this invention is designed to be a three-way interface device, one end being an oxygen input interface, another end being a laser fiber import interface, the final one being a laser-oxygen two-in-one outlet. Therefore, the airtightness cannot be guaranteed, and the production process is complex, not conducive to the user's tong-term use; the oxygen outlet of this invention is directly arranged on the body of the apparatus, where the environment is rich in oxygen and easy to breed bacteria, and the oxygen output interface on the body of the apparatus is inconvenient to be cleaned, which thus causes bacteria to be inhaled inevitably; the light guide form of an optical fiber is selected for the laser irradiation of this invention, but the optical fiber is easy to be broken and suffers light loss in the daily use, increasing the use cost and instability; the accessories of this invention include the laser-oxygen two-in-one therapeutic head as well as the separate oxygen pipeline and optical fiber needle, which not only increase the user's use cost and maintenance procedures but also make the user have no freedom of choice with this solidified two-in-one therapeutic head, only allowing one person to accept the laser irradiation while inhale oxygen. Besides, a professional doctor is needed to use the optical fiber needle, and in specific circumstances blood irradiation is needed by puncturing the blood vessel to achieve the therapeutic purposes. The drawbacks of this therapy are lossy and prone to infection, not conducive to long-term adherence. This laser blood oxygen machine is not provided like a pure oxygen machine with an atomizing device that can release medicament, because the atomizing device requires the use of high-pressure oxygen to break up the medicament therein and plays the role of decompression; if the oxygen output and atomization output are performed simultaneously on one machine, and if a user, due to misoperation, presses the atomization button but connects the common oxygen output head, there will be the problem of direct output of the high-pressure oxygen to the user's nasal or oral cavity.

BRIEF SUMMARY OF THE INVENTION

The technical problem to be solved by the present invention is to eliminate the shortages of the above products by providing a semiconductor laser blood oxygen therapeutic apparatus, which is of a highly integrated design, can be used simultaneously at multiple sites, for multiple purposes and for many persons, is easy for the patient to maintain, has enough security, is suitable for long-term treatment, and is suitable for the patient to use at home. The semiconductor laser blood oxygen therapeutic apparatus comprises: a laser generator, a host shell, a control panel, a controller within the host shell, an oxygen generator, a relief pressure valve, and a silencer; a terminal outside the host, the terminal including an oxygen output terminal and a laser irradiating terminal; an oxygen production channel within the host is composed of the oxygen generator, the relief pressure valve and an internal oxygen pipeline that are connected with each other successively; characterized in that: the laser generator is located in a therapeutic terminal rather than in the host shell like the laser generator of the existing semiconductor laser blood oxygen therapeutic apparatus, and then laser is outputted through the easily damaged optical fiber.

The therapeutic terminal and the host are provided respectively with a mating connector that can be freely connected and disconnected, which also changes the usual way of stretching directly from the host out of the terminal; the therapeutic terminal further includes an ozone output terminal, which includes an oxygen absorbing device and a laser-oxygen two-in-one therapeutic device; the laser irradiating terminal includes a laser-oxygen two-in-one therapeutic device, a nasal-clip type laser therapeutic device, and a wrist-type laser therapeutic device, the wrist-type laser therapeutic machine being able to perform laser irradiation of the wrist radial artery or Neiguan point; the laser-oxygen two-in-one therapeutic device is provided with a two-in-one nasal clip, which is provided with two jackets used to embed a nasal clip oxygen head or the nasal-clip type laser therapeutic device, the nasal clip oxygen head or the nasal-clip type laser therapeutic device being each provided with an independent connecting wire and connecting head, the two-in-one nasal clip completely changing the therapeutic method with the laser and oxygen terminals compulsively integrated into one.

The wrist-type laser therapeutic device realizes the treatment by the vitro irradiation of the wrist radial artery or Neiguan point, instead of by using optical fiber needle to puncture the skin, which reduces pain and avoids the cross infection risk.

The oxygen absorbing device includes an atomization pressure decreasing device that is usually detachable. The oxygen absorbing device provided with the atomization pressure decreasing device is required to input the high-pressure oxygen for atomization effect and breaking up the possible medicament in the atomization pressure decreasing device, and the oxygen absorbing device not provided with the atomization pressure decreasing device can only output the low-pressure oxygen. However, if the oxygen absorbing device that can only input the low-pressure oxygen is connected but the atomization button is pressed due to the user's misoperation, the high-pressure oxygen will be outputted directly to the oxygen outlet, thus resulting in an accident. In order to avoid this, the present invention abandons the mode of user artificial delay recognition, but provides the host with a security identifying device which is partly mounted to an oxygen output interface and identifies the external atomization pressure decreasing device.

An ozone generating cabin, provided inside with an ozonizer, is connected between the relief pressure valve and the humidifying bottle.

The therapeutic terminal can be freely connected to and disconnected from the host through connection of a connecting head in a plug form with the corresponding socket on the control panel, or through connection of a connecting head in a metal sheet form with the corresponding terminal on the host shell. In fact, we can also see from everyday life a variety of conductor connection ways, such as a magnetic connection method, a wire connection method using a metal clip, or a box-type connection method with a built-in spring.

The host shell and the control panel are provided with multiple sockets or terminals connected with the therapeutic terminal, the receptacles or terminals on the host being connected with the interface of the controller in the host through a wire. Such a setting can make many persons use the product at the same time.

The oxygen output terminal is connected with the oxygen output interface of the host shell through the oxygen conveying pipe or the humidifying bottle.

The host shell and the control panel are provided with multiple sockets or terminals connected with the therapeutic terminal, the sockets or terminals on the host being connected with the interface on the main control board in the host through a wire.

The control panel is provided with a panel key, an overhigh air pressure output indicator, an oxygen density limit alarm indicator, a flowmeter, a flow regulation button and a laser terminal external interface. Besides, inside the internal oxygen pipeline is arranged an oxygen density sensor.

The security identifying device in the host includes an atomization adapter and the oxygen output interface mounted in the host; the atomization adapter has an output port that is connected with the oxygen absorbing device having the atomization pressure decreasing device and an input port that is provided with a conductive metal ring; the oxygen output interface is provided with two pieces of conductive metal shrapnel, which are connected into a panel key loop of the atomization button in series with the conductive metal ring electrically connected with them, forming an access signal induction loop of the atomization pressure decreasing device, thus constituting the security identifying device of the external atomization pressure decreasing device.

The oxygen mask may be provided with an atomizing device, which can usually also have the function of mixing medicament and can provide an oxygen atomization treatment for a patient with respiratory diseases who needs the medicament atomization treatment; the atomizing device may be a venturi cup, which has an input and output interface detachably connected with the oxygen pipeline of the oxygen mask. The venturi cup itself has a function of accompanying atomization of the built-in medicament, and a function of pressure reduction of the high-pressure gas. The oxygen atomization can also be performed directly without mixture of the medicament.

The ozonizer includes an ozone generating ceramic sheet and an ozone generating circuit module; the ozone generating ceramic sheet, located inside the ozone generating cabin, is electrically connected with an output port of the ozone generating circuit module through a wire; the ozone generating circuit module is connected at its power supply end in series with a key switch mounted on the control panel. When the switch is in the off state and there is no ozone to be outputted, the key can be pulled out; when the switch is in the on state and there is ozone to be outputted, the key cannot be pulled out.

The atomizing device is provided on the panel key with a cooperating atomization button. The parts on the control panel will all be connected with the controller to be as the signal input or output port of the controller, with the program cooperating with the corresponding function.

The host is provided with a front caster and a rear caster for convenient drag. Both this feature and the above-mentioned feature that the therapeutic terminal can be freely connected to and disconnected from the host make the complete apparatus easier to move and carry.

The ozone output terminal is provided with an aeration stone, which can be arranged at an outlet end of any of the oxygen output pipes.

The beneficial effects of the present invention are as follows:

1. The present invention adopts an integrated design. Because the normal-pressure oxygen that can be inhaled directly by the human being and the no-decompression high-pressure oxygen used for atomization are outputted through the same channel, the present invention adopts the following multiple protection measures in order to prevent the high-pressure oxygen from being directly inhaled by the user unpredictably:

(1) The "oxygen" and "atomization" output buttons are set independently, respectively; (2) before the command of "atomization" is executed, the atomization adapter special for atomization has to be mounted to the oxygen outlet of the host. When the atomization adapter embedded with a conductive metal ring is connected into the oxygen outlet of the host, the two pieces of conductive metal shrapnel not connected are then connected to the oxygen outlet of the host; here only when the atomization button command line is in the on state, can the "atomization" button be operated. Because in the present invention the control mode that the host automatically recognizes the oxygen absorbing terminal is adopted for the oxygen atomization output, such situation is thus prevented that the user suffers oxygen discomfort in the oxygen mode when he/she touches the oxygen atomization control button accidentally, ensuring safe and comfort oxygen inhalation for the user.

2. The output of the present invention includes the oxygen output, the oxygen atomization output of mixable medicaments and the laser output to achieve the multiplied curative effects, as well as the ozone output to play a role of disinfection of the humidifying bottle, the oxygen pipeline and the oxygen absorbing terminal, and other functions.

3. The host of the present invention is provided itself in its oxygen channel with an ozonizer. Most of the methods of preparing ozone are realized by electric shock of the oxygen in the air for production of ozone. First, because the density of the oxygen in the air is about 21%, the density of ozone generated by electric shock is inevitably low. Second, with the density of the nitrogen in the air being about 78%, human carcinogenic nitrogen compounds may be generated after electric shock; this technology, through connecting the ozone generating cabin to the oxygen production device, has an oxygen source for preparing ozone that is the high-density oxygen with a density above 90%; oxygen, when passing by an ozone generating sheet in the ozone generating chamber, under the condition that the ozone function is in action, can then be used to produce the high-density ozone, thus also avoiding the risk of producing the nitrogen compounds; the ozone produced can disinfect the humidifying bottle, the oxygen pipeline and the oxygen absorbing terminal, and can facilitate its use by the user in daily life. The present invention adopts an integrated design. Because both oxygen and ozone pass by the ozone generating chamber (that is, when the ozone function is not in action, the ozone generating cabin is only an oxygen channel), in order to avoid the risk possibly resulted from the user's misoperation, the present invention adopts a key switch with the on-off function on the control panel; when the switch is in the off state and there is no ozone to be outputted, the key can be pulled out, and when the switch is in the on state and there is ozone to be outputted, the key cannot be pulled out.

4. The laser output and oxygen output devices of the present invention can be used either in combination or alone, especially through a simply manufactured two-in-one nasal clip, making the user convenient to freely distribute and use as well as maintain. The present invention thoroughly changes the common compulsive use mode where the laser and oxygen are solidified into one, and the oxygen or laser terminal can be replaced conveniently when it has malfunction.

5. The laser generator of the present invention is located inside the laser therapeutic terminal rather than inside the host as usual; the laser emitted by the common laser generator from within the host is outputted to the therapeutic terminal through expensive and easily damaged optical fiber with light loss. The improvements of the present invention thus greatly reduce the failure rate of the complete apparatus.

6. The present invention adopts an intelligence control mode. If in the process of operation the air pressure of the output port is too high or the density of oxygen exceeds the limit due to such problems as bending and obstruction of the oxygen pipeline, the control system will alarm and automatically stop running, increasing the safe coefficient; meanwhile, when the power is off in the process of operation, the system will automatically place the functional components in an off state in advance, so as to avoid unexpected situations when the power is on again.

7. The therapeutic terminal and host of the present invention can conveniently be connected to or disconnected from each other freely; and the host is provided with a front caster and a rear caster for convenient drag, making the complete apparatus easy to be moved and carried.

8. The present invention is highly integrated in function, but has a very small volume, allowing the user to use the apparatus whenever and wherever possible so long as the power supply is available.

LIST OF REFERENCE NUMBERS

Figure 1:
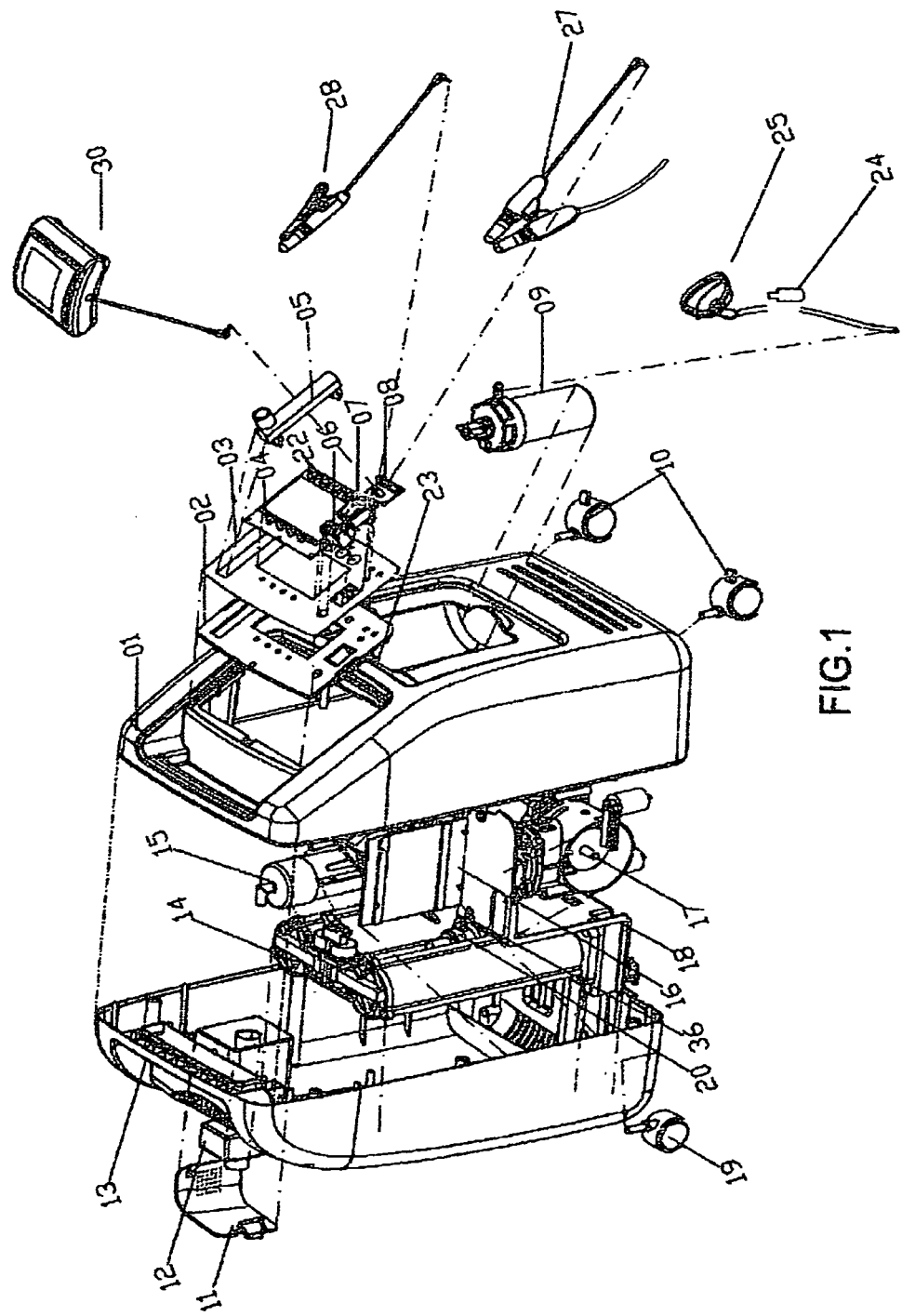
FIG. 1 is an exploded structural schematic view of the present invention.

1. Host shell; 2. control panel shell; 3. paster; 4. control panel; 5. flowmeter; 6. overload protection device; 7. power switch; 8. laser terminal external interface; 9. humidifying bottle; 10. front caster; 11. silencer cover; 12. sound filter; 13. bottom shell; 14. oxygen generator; 15. silencer; 16. main control board; 17. compressor; 18. hardware support; 19. rear caster; 20. relief pressure valve; 21. controller; 22. panel key; 23. oxygen output interface; 24. atomization pressure decreasing device; 25. oxygen absorbing device; 26. nasal clip oxygen head; 27. laser-oxygen two-in-one therapeutic device; 28. nasal-clip type laser therapeutic device; 30. wrist-type laser therapeutic device; 31. two-in-one nasal clip; 32. host; 33. jacket; 34. therapeutic terminal; 35. oxygen density sensor; 36. ozone generating cabin; 37. pressure sensor; 38. conductive metal shrapnel; 39. conductive metal ring; 40. atomization adapter output port; 41. key switch; 42. ozone generating circuit module; 43. ozone generating ceramic sheet; 44. ozone generating cabin input port; 45. ozone generating cabin output port; 46. atomization button; 47. key switch; 48. ozone output terminal; and 49. aeration stone.

DETAILED DESCRIPTION OF THE INVENTION

An introduction is first made of the basic principle of the laser blood oxygen therapeutic apparatus.

The laser generator, using the red laser of 650 nm in wavelength, irradiates the nasal cavity, wrist radial artery or Neiguan point, all of which are the parts of the human being with thin skin tissue, densely-distributed blood vessels and high blood flow, making the red cells within the blood vessels and capillaries maximize the absorption of the photon energy, restoring the oxygen carrying capacity and deformation performance of red blood cells, improving the hemorheology parameters.

The oxygen production system, using the zeolite molecular sieve as the adsorbent, compresses the air with an oil-free compressor, and adsorbs the nitrogen in the air through a pressure swing adsorption (PSA) technology, thus producing the medical oxygen with a density 90%; inhalation of oxygen can increase the pulmonary ventilation effect and effectively improve the anoxic condition, and improve the oxygen content, both of which combined together can have a multiplied therapeutic effect for a variety of hypoxic ischemic cardiovascular and cerebrovascular diseases. The oxygen atomization system, using the high-speed oxygen to convert the medicament into fine aerosol, can be used for the treatment of respiratory system diseases for the patient's inhalation trachea, bronchus and alveoli. Besides, the patient can continuously be provided with adequate oxygen during the oxygen driven atomization inhalation therapy, vapor inhalation having small irritation to the patient's respiratory tract, making the patient feel comfortable. The present invention achieves a multiplied therapeutic effect by effectively combining the laser irradiation system, the molecular sieve oxygen production system and the oxygen atomization system.

Meanwhile, the present invention uses the ozone produced with the high-density oxygen for disinfection of the oxygen output channel and each therapeutic terminal of the apparatus, as well as for other purposes. The host of the present invention is provided itself in its oxygen channel with an ozonizer. Most of the methods of preparing ozone are realized by electric shock of the oxygen in the air for production of ozone. First, because the density of the oxygen in the air is about 21%, the density of ozone generated by electric shock is inevitably low; second, with the density of the nitrogen in the air being about 78%, human carcinogenic nitrogen compounds may be generated after the electric shock. The present invention, through connecting the ozone generating cabin to the oxygen production device, has an oxygen source for preparing ozone that is the high-density oxygen with a density above 90%; oxygen, when passing by the ozone generating sheet in the ozone generating chamber, under the condition that the ozone function is in action, can then be used to produce the high-density ozone, thus also avoiding the risk of producing the nitrogen compounds; the ozone produced can disinfect the humidifying bottle, the oxygen pipeline and the oxygen absorbing terminal, and can facilitate its use by the user in daily life.

Figure 2:
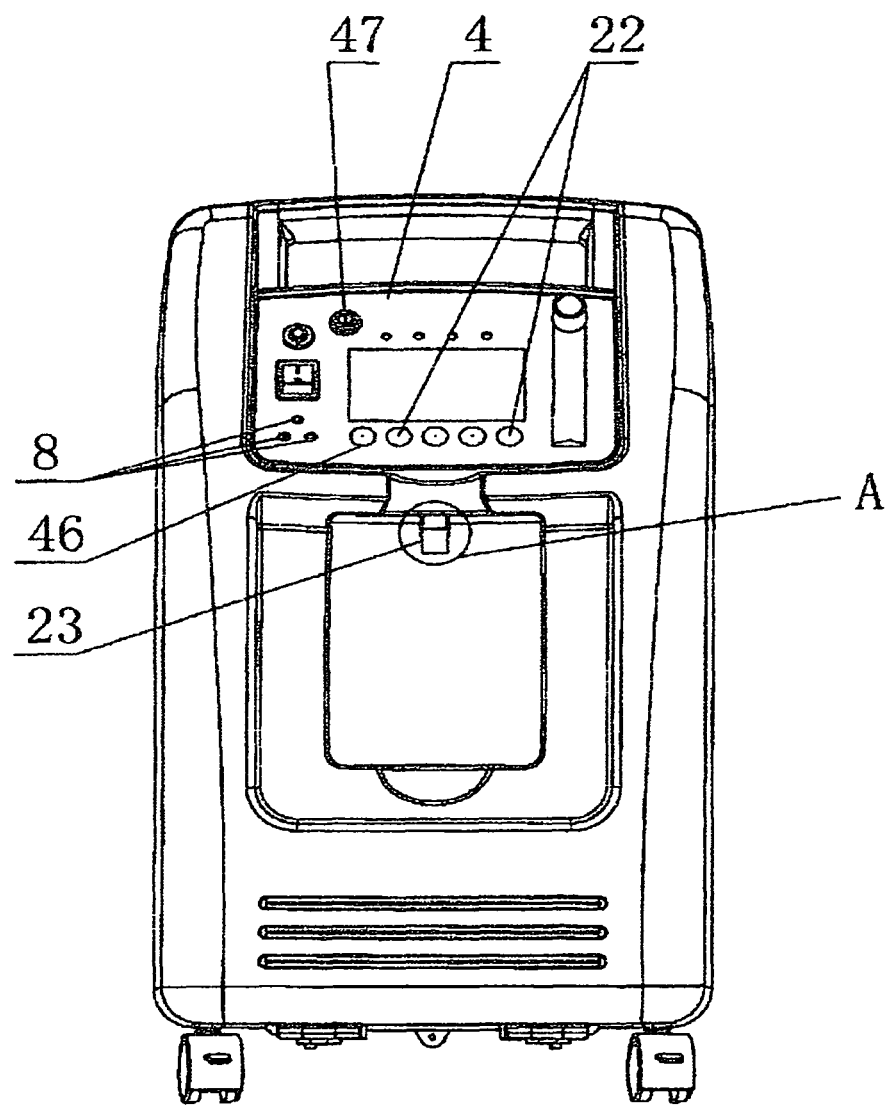
FIG. 2 is a front structural schematic view of the host of the example of the present invention.
Figure 3:
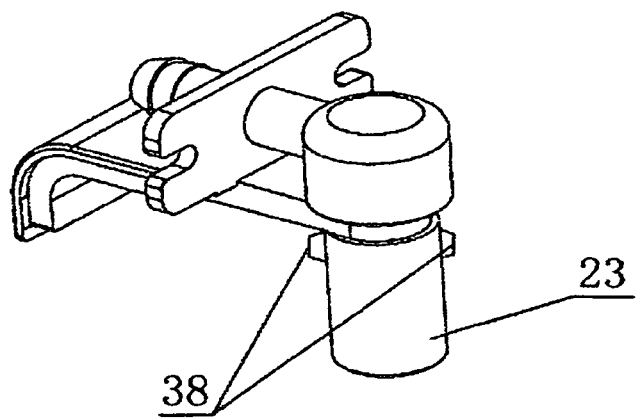
FIG. 3 is an enlarged stereoscopic structural schematic view of the oxygen interface at the position A of FIG. 2.
Figure 4:
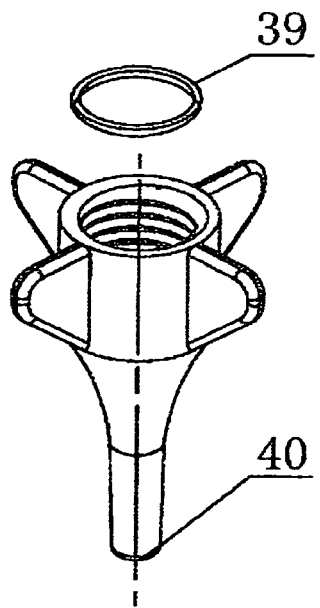
FIG. 4 is an exploded structural stereoscopic view of the atomization adapter.
Figure 5:
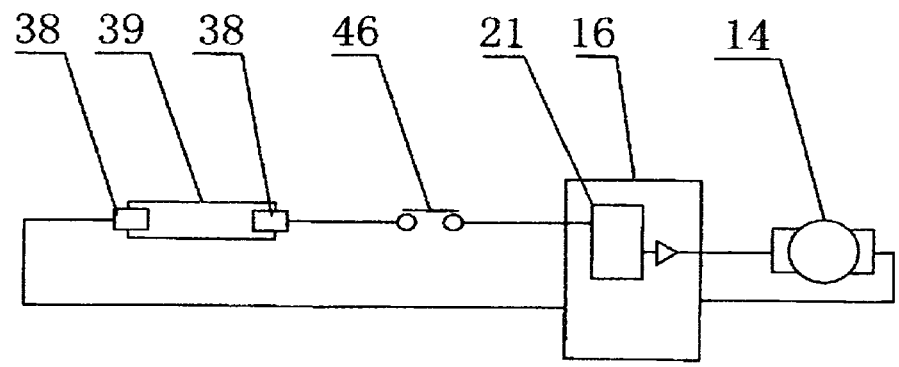
FIG. 5 is a block diagram of the principle of the atomization control circuit.
Figure 8:
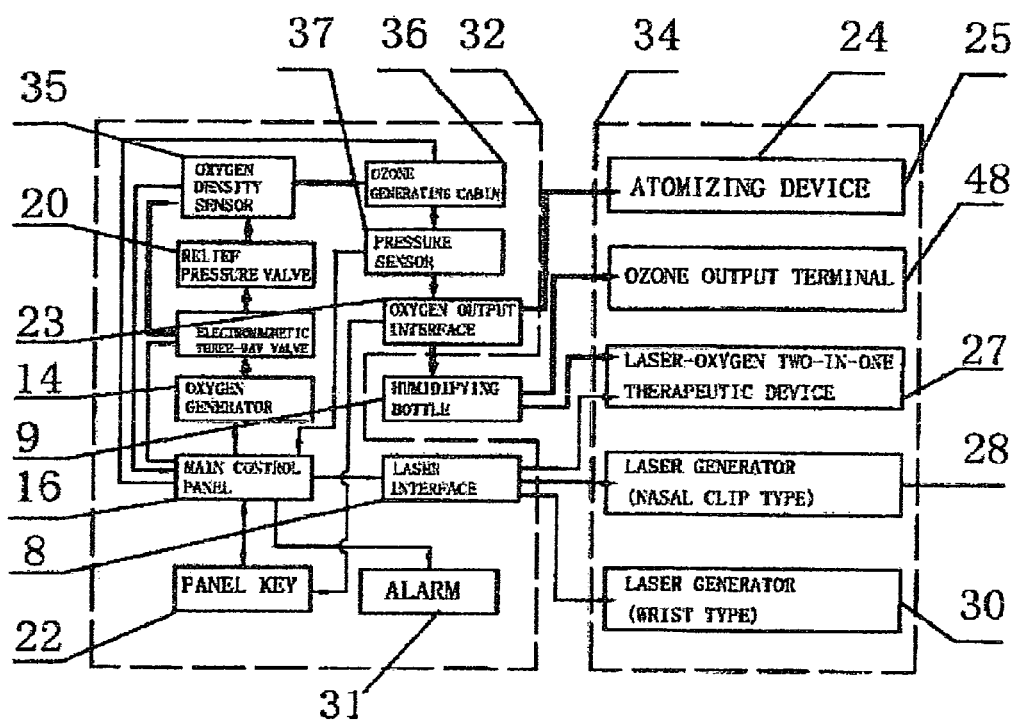
FIG. 8 is a block diagram of the electrical and structural principle function of the present invention, where the fine line indicates the control signal line while the thick line indicates the air channel.

The specific ways of realization and implementation will be described below with reference to examples and drawing:

The semiconductor laser blood oxygen therapeutic apparatus as shown in FIGS. 1, 2 and 8 includes a laser generator, a host shell 1, a control panel 4, a main control board 16 within the host shell, an oxygen generator 14, a relief pressure valve 20, a silencer 15, a humidifying bottle 9, and a therapeutic terminal 34 outside the host, the therapeutic terminal being an oxygen output terminal and a laser irradiating terminal; an oxygen production channel within the host is composed of the oxygen generator 14, an electromagnetic three-way valve, a relief pressure valve 20 and an internal oxygen pipeline that are connected with each other successively; the laser generator is located in a therapeutic terminal 34, rather than in the host shell like the laser generator of the existing semiconductor laser blood oxygen therapeutic apparatus; and then the laser is outputted through the easily damaged optical fiber. The failure rate of the complete apparatus is thus greatly reduced due to elimination of the expensive and easily damaged optical fiber.

The therapeutic terminal 34 and the host 32 are provided with a mating connector that can be freely connected and disconnected, respectively; which also changes the usual way of stretching directly from the host out of the terminal, making the complete apparatus easier to be moved and carried; the oxygen output terminal includes an oxygen absorbing device 25 and a laser-oxygen two-in-one therapeutic device 27; the laser irradiating terminal includes a laser-oxygen two-in-one therapeutic device 27, a nasal-clip type laser therapeutic device 28, and a wrist-type laser therapeutic device 30.

Figure 7:
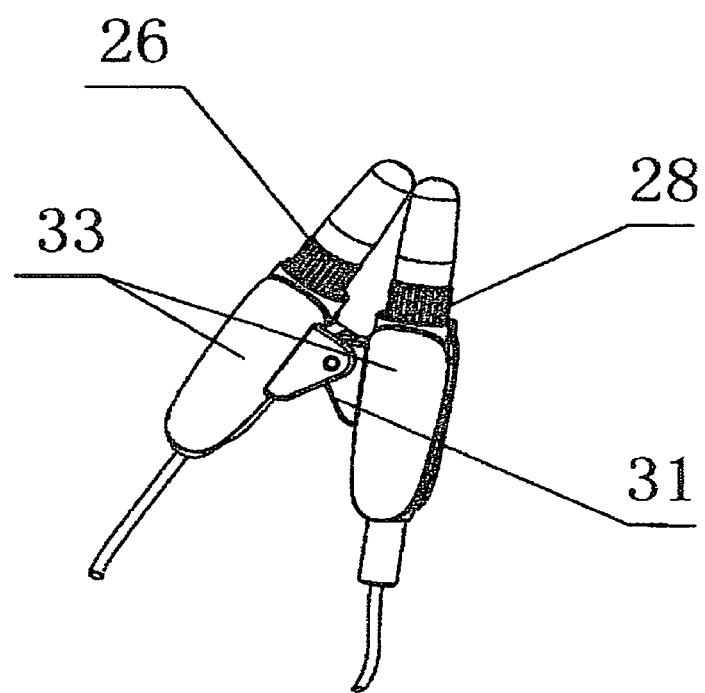
FIG. 7 is a schematic view of the two-in-one nasal clip.

As shown in FIG. 7, the laser-oxygen two-in-one therapeutic device 27 is provided with a two-in-one nasal clip 31, which is provided with two jackets 33 used to embed the nasal clip oxygen head 26 or the nasal-clip type laser therapeutic device 28, the nasal clip oxygen head 26 or the nasal-clip type laser therapeutic device 28 each being provided with an independent connecting wire and connecting head, making the user convenient to freely distribute and use as well as maintain. The present invention thoroughly changes the common compulsive use mode where the laser and oxygen are solidified into one, and the oxygen or laser terminal can be replaced conveniently when it has malfunction.

As shown in FIG. 1, the oxygen absorbing device 25 includes an atomization pressure decreasing device 24, which can detachably be connected to the oxygen absorbing device. The oxygen absorbing device provided with the atomization pressure decreasing device is required to input the high-pressure oxygen for atomization effect and breaking up the possible medicament in the atomization pressure decreasing device, and the oxygen absorbing device not provided with the atomization pressure decreasing device can only output the low-pressure oxygen. However, if the oxygen absorbing device that can only input the low-pressure oxygen is connected but the atomization button is pressed due to the user's misoperation, the high-pressure oxygen will be outputted directly to the oxygen outlet, thus resulting in an accident. In order to avoid this, the present invention abandons the mode of user artificial delay recognition, but provides the host 32 with a security identifying device which is partly mounted to an oxygen output interface 23 and identifies the external atomization pressure decreasing device 24.

Figure 6:
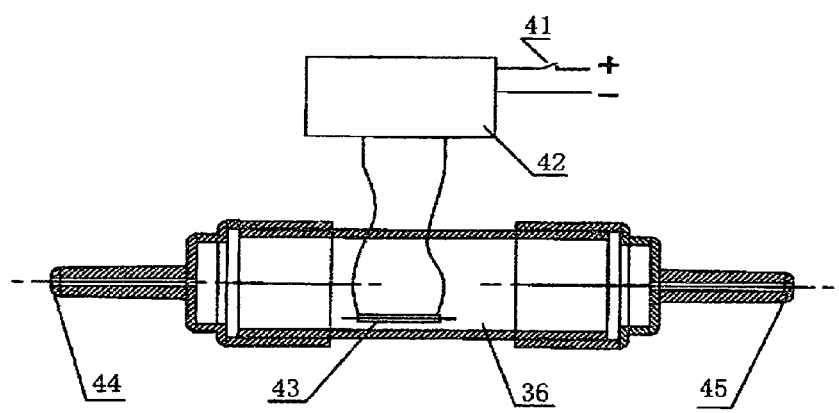
FIG. 6 is a structural principle diagram of the ozonizer.

As shown in FIG. 6, an ozone generating cabin 36, provided inside with an ozonizer, is connected between the relief pressure valve 20 and the oxygen output interface 23. The ozonizer includes an ozone generating ceramic sheet 43 and an ozone generating circuit module 42; the ozone generating ceramic sheet 43, located inside the ozone generating cabin 36, is electrically connected with an output port of the ozone generating circuit module 42 through a wire; the ozone generating circuit module 42 is connected at its power supply end in series with a key switch 41 with the on-off function mounted on the control panel 4. When the switch is in the off state and there is no ozone to be outputted, the key can be pulled out, and when the switch is in the on state and there is ozone to be outputted, the key cannot be pulled out.

As shown in FIGS. 1 and 2, the oxygen output terminal is connected with the oxygen output interface 23 of the host shell or the oxygen output interface of the humidifying bottle 9 through the oxygen conveying pipe. If the atomization pressure decreasing device is connected externally, it can be connected directly to the oxygen output interface 23 prior to the humidifying bottle without going through the humidifying bottle.

The host shell and the control panel are provided with multiple sockets or terminals connected with the therapeutic terminal, the sockets or terminals on the host being connected with an interface on the main control board 16 in the host through a wire. Such a setting can make many persons use the product at the same time.

As shown in FIG. 2, the control panel is provided with a panel key 22, an overhigh air pressure output indicator, an oxygen density limit alarm indicator, a flowmeter 5, a flow regulation button and a laser terminal external interface 8.

As shown in FIGS. 2-5, the security identifying device in the host includes the atomization adapter and the oxygen output interface 23 mounted in the host; the atomization adapter has an output port 40 that is connected with the oxygen absorbing device provided with the atomization pressure decreasing device 24, and an input port that is provided with a conductive metal ring 39; the oxygen output interface 23 is provided with two pieces of conductive metal shrapnel 38, which are connected into a panel key loop of the atomization button 46 in series with the conductive metal ring 39 electrically connected with them, forming an access signal induction loop of the atomization pressure decreasing device, thus constituting the security identifying device of the external atomization pressure decreasing device 24.

The atomization pressure decreasing device 24 can be a venturi cup, which has an input and output interface detachably connected with the oxygen pipeline of the oxygen absorbing device. The venturi cup itself has a function of accompanying atomization of the built-in medicament, and a function of pressure reduction of the high-pressure gas. The outputted oxygen can also be atomized directly without putting the medicament inside.

The ozone output terminal 48 is provided with an aeration stone 49, which can be arranged at an outlet end of any of the oxygen output pipes. The aeration stone can buffer the high output of airflow and air bubbles, making the gas more easily to be dissolved in water.

As shown in FIG. 1, the host mainly includes the oxygen production section and control section; the oxygen production section includes the oxygen generator 14, the air compressor 17 cooperating with the oxygen production, the oxygen humidifying bottle 9 at the output stage, the silencer 15 for eliminating noise, the sound filter 12, and the silencer cover 11; the control section includes the controller 21 on the main control board 16, the oxygen flowmeter 5 provided with a flow regulation button, the relief pressure valve 20 controlled by the main control board and connected from the oxygen generator, and the control panel 4 showing the input and output states, the control panel being provided with the panel key 22, the power switch 7, the power supply state indicator and the laser output jack.

The block diagram of the connection structure of the host and the connection thereof with the therapeutic terminal is as shown in FIG. 8. It can be seen from FIG. 8 that the panel key 22, as an instruction issuing end, is electrically connected with the input interface of the main control board 16 through a wire; the controller controls the operation state of the oxygen generator 14 and relief pressure valve 20 through the driving device; the relief pressure valve 20, according to the state of use, does not reduce pressure under the atomization instruction, and is directly through to the oxygen output interface 23; the relief pressure valve 20, under the oxygen output instruction, outputs oxygen to the ozone generating cabin 36 after relief pressure is started; an oxygen density sensor 35 is located between the relief pressure valve 20 and the ozone generating cabin 36, which is connected to the oxygen output interface 23 on the host; an output pressure sensor 37 of the output oxygen is located prior to the oxygen output interface 23, which is connected with the dismountable humidifying bottle 9 outside the host; the oxygen outputted by the humidifying bottle reaches the nasal clip oxygen head 26 or the oxygen absorbing device 25 through the oxygen conveying pipe of the therapeutic terminal; and multiple laser terminal external interfaces 8 on the control panel can be used for multiple sites and persons simultaneously through the laser therapeutic device. The laser therapeutic device can be divided into an independent laser for irradiation of the nasal cavity, i.e. a nasal-clip type laser therapeutic device 28, or a part of the laser-oxygen two-in-one therapeutic device, and a laser for irradiation of the wrist radial artery and Neiguan point, i.e. a wrist-type laser therapeutic device 30.

Figure 9:
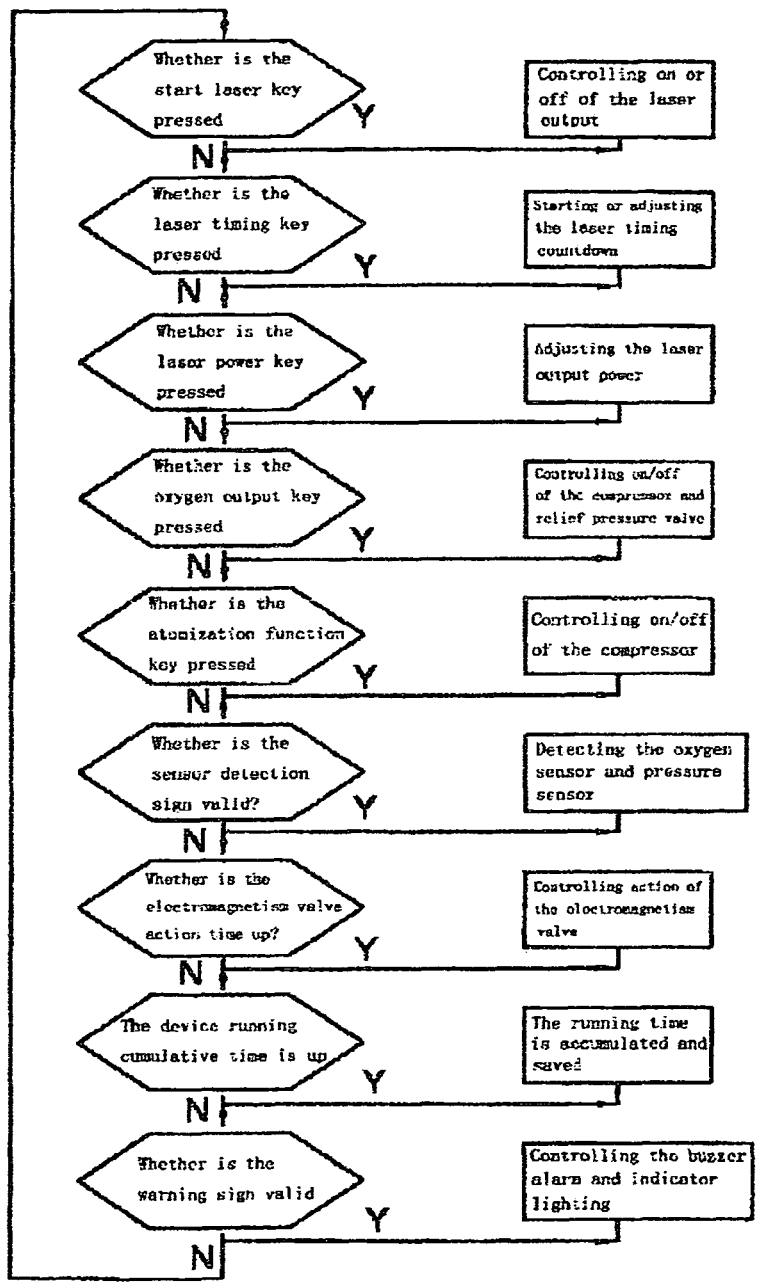
FIG. 9 is a flow chart of the control section of the present invention.

For the total control and coordination of the present invention, the controller monitors the complete apparatus system in the different power supply environments; if in the process of operation the voltage is high or low and the power is off, the control system will automatically stop running, increasing the safe coefficient; meanwhile, the control of the controller on the whole laser and oxygen depends on the user's operation of the control panel according to the program setting, and the specific flow block diagram is as shown in FIG. 9; the system scans sequentially each key on the control panel, and executes the corresponding program. The start laser key, here being a logic switch controlling on or off of the laser, is pressed to control on or off of the laser, with the controller issuing the instruction for the on or off of the laser. Otherwise the detection is made whether the laser timing key is pressed, and if the laser timing key is pressed the countdown of the laser timer is started or adjusted, with the timer started at the same time, the timing program being used to turn off the laser output when the time is up. Otherwise the detection is made whether the laser power key is pressed, and if the laser power key is pressed the laser output power is adjusted in the limited range according to the keyboard instruction. Otherwise the detection is made whether the oxygen output key is pressed, and if the oxygen output key is pressed the compressor is controlled to be turned on or off; here the oxygen output key is also a logic switch for control of the oxygen output or closure, giving a control signal sent out by the main control board to the controller. Otherwise the detection is made whether the atomization function key is pressed, and if the atomization function key is pressed the atomization function is controlled to be turned on or off; especially the unique atomization function of the present invention is that when the oxygen absorbing device provided with the atomization function device is used at the therapeutic terminal, because the atomization function requires breaking up the possible medicament in the atomization function device with high pressure and meanwhile reducing the pressure, the system here requires closure of the function of the relief pressure valve in the host, and the high-pressure oxygen is directly outputted, while the atomization key loop is connected with the atomization identifying device in serial, thus guaranteeing output of the low-pressure oxygen at the output port. Then the system scanning sensor detects whether the time is up, and if the sensor detects that the time is up the oxygen sensor and pressure sensor are then detected, the system making a timed detection of the state of the sensor as the feedback of the state of use. Otherwise the detection is made whether the electromagnetic valve action time is up, and if the electromagnetism valve action time is up the electromagnetism valve is controlled to act. Otherwise the detection is made whether the device running cumulative time is up, and if the device running cumulative time is up the running time is accumulated and saved, until the total set running time is up, when the device is stopped. Then the detection is made whether the warning sign is valid, and if the warning sign is valid the buzzer alarm is controlled to alarm and the indicator is lighted to alarm.

What is claimed is:

1. A semiconductor laser blood oxygen therapeutic apparatus, comprising:
a host shell, a control panel, a controller within the host shell, an oxygen generator, a relief pressure valve, and a silencer; a terminal outside a host, the terminal including an oxygen output terminal and a laser irradiating terminal;
an oxygen production channel within the host is composed of the oxygen generator, the relief pressure valve and an internal oxygen pipeline that are connected with each other successively; characterized in that the semiconductor laser blood oxygen therapeutic apparatus further comprises a therapeutic terminal (34), which further includes an ozone output terminal (48), the therapeutic terminal and the host (32) being respectively provided with a mating connector that can be freely connected and disconnected; the oxygen output terminal includes an oxygen absorbing device (25) and a laser-oxygen two-in-one therapeutic device (27); the laser irradiating terminal includes the laser-oxygen two-in-one therapeutic device (27), a nasal-clip type laser therapeutic device (28), and a wrist-type laser therapeutic device (30); the laser-oxygen two-in-one therapeutic device (27) is provided with a two-in-one nasal clip (31), which is provided with two jackets (33) used to embed a nasal clip oxygen head (26) or the nasal-clip type laser therapeutic device (28), the nasal clip oxygen head (26) or the nasal-clip type laser therapeutic device (28) each being provided with an independent connecting wire and connecting head; the oxygen absorbing device (25) includes an atomization pressure decreasing device (24), the host (32) being provided with a security identifying device which is partly mounted to an oxygen output interface (23) and identifies the atomization pressure decreasing device (24); an ozone generating cabin (36), provided inside with an ozonizer, is connected between the relief pressure valve (20) and a humidifying bottle (9).

2. The semiconductor laser blood oxygen therapeutic apparatus according to claim 1,
characterized in that: the oxygen output terminal is connected with the oxygen output interface (23) of the host shell through an oxygen conveying pipe or the humidifying bottle (9).

3. The semiconductor laser blood oxygen therapeutic apparatus according to claim 1,
characterized in that: the host shell and the control panel are provided with multiple sockets or terminals connected with the therapeutic terminal, the sockets or terminals on the host being connected with an interface on a main control board (16) in the host through a wire.

4. The semiconductor laser blood oxygen therapeutic apparatus according to claim 1 or 3,
characterized in that: the control panel is provided with a panel key (22), an overhigh air pressure output indicator, an oxygen density limit alarm indicator, a flowmeter (5), a flow regulation button and a laser terminal external interface (8).

5. The semiconductor laser blood oxygen therapeutic apparatus according to claim 1,
characterized in that: the security identifying device in the host includes an atomization adapter and the oxygen output interface (23) mounted in the host; the atomization adapter has an output port (40) that is connected with the oxygen absorbing device provided with the atomization pressure decreasing device (24), and an input port that is provided with a conductive metal ring (39); the oxygen output interface (23) is provided with two pieces of conductive metal shrapnel (38), which are connected into a panel key loop of the atomization button (48) in series with the conductive metal ring (39) electrically connected with them, forming an access signal induction loop of the atomization pressure decreasing device, thus constituting the security identifying device of the atomization pressure decreasing device (24).

6. The semiconductor laser blood oxygen therapeutic apparatus according to claim 1 or 5,
characterized in that: the atomization pressure decreasing device (24) is a venturi cup, which has an input and output interface detachably connected with the oxygen pipeline of the oxygen absorbing device.

7. The semiconductor laser blood oxygen therapeutic apparatus according to claim 1,
characterized in that: the ozonizer includes an ozone generating ceramic sheet (43) and an ozone generating circuit module (42); the ozone generating ceramic sheet (43), located inside the ozone generating cabin (36), is electrically connected with an output port of the ozone generating circuit module (42) through a wire; the ozone generating circuit module (42) is connected at its power supply end in series with a key switch (41) mounted on the control panel (4).

8. The semiconductor laser blood oxygen therapeutic apparatus according to claim 1,
characterized in that: the atomizing device (24) is provided on the panel key (22) with a cooperating atomization button.

9. The semiconductor laser blood oxygen therapeutic apparatus according to one of claims 1, 2 and 3,
characterized in that: the host is provided with a front caster (10) and a rear caster (19) for convenient drag.

10. The semiconductor laser blood oxygen therapeutic apparatus according to claim 1,
characterized in that: the ozone output terminal (48) is provided with an aeration stone (49), which can be arranged at an outlet end of any oxygen output pipes.

\* \* \* \* \*